United States Patent [19]

Abou-Gharbia et al.

[11] Patent Number: 4,709,027
[45] Date of Patent: Nov. 24, 1987

[54] BICYCLIC SPIROSULFONIMIDES WITH PSYCHOTROPIC ACTIVITY

[75] Inventors: Magid A. Abou-Gharbia, Wilmington, Del.; Guy A. Schiehser, Malvern, Pa.

[73] Assignee: American Home Products Corporation, New York, N.Y.

[21] Appl. No.: 878,448

[22] Filed: Jun. 25, 1986

[51] Int. Cl.$^4$ .......................................... C07D 417/06
[52] U.S. Cl. .......................................... 544/6; 544/8; 540/453; 540/454; 540/488; 540/575; 540/489
[58] Field of Search ............... 544/8, 6; 540/453, 454, 540/488, 575, 489

[56] References Cited

U.S. PATENT DOCUMENTS 4,558,045 12/1985 Hargreaves et al. ................. 544/8

Primary Examiner—Richard A. Schwartz
Assistant Examiner—J. Richter
Attorney, Agent, or Firm—George Tarnowski

[57] ABSTRACT

There are disclosed compounds of the formula

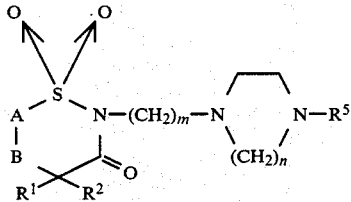

wherein
$R^1$ and $R^2$ are each, independently, hydrogen or lower alkyl, or $R^1$ and $R^2$ taken together represent

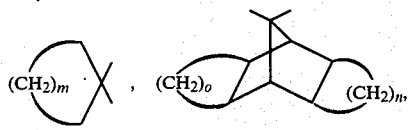

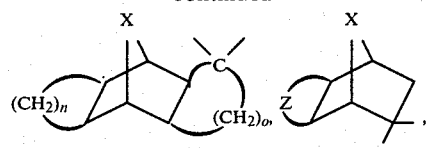

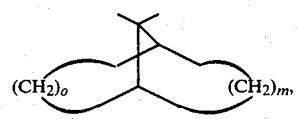

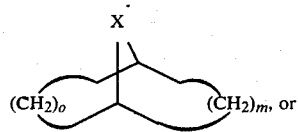

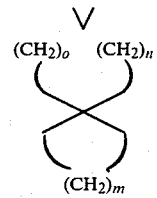

A is O or $NR^3$;
B is —$(CH_2)_n$—,

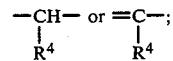

$R^3$ is hydrogen or lower alkyl;
$R^4$ is hydrogen, lower alkyl, aryl of 6–12 carbon atoms or halo;
$R^5$ is unsubstituted or substituted phenyl, 2-pyridinyl, 2-pyrimidinyl, 2-pyrazinyl or 3-pyridazinyl, where the substituents are selected from the group lower alkyl, lower alkoxy, halo, cyano, nitro and trifluoromethyl;
Z is —$(CH_2)_n$— or vinylene;
X is lower alkylene, vinylene or O;
m is 2–5;
n is 1–3;
o is 1–5;

and the pharmaceutically acceptable salts thereof and their use as antipsychotic/anxiolytic agents having a low liability for extrapyramidal side effects.

5 Claims, No Drawings

BICYCLIC SPIROSULFONIMIDES WITH PSYCHOTROPIC ACTIVITY

This invention relates to novel compounds having antipsychotic activity and being characterized by the general formula

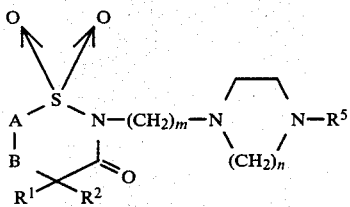

wherein

R[1] and R[2] are each, independently, hydrogen or lower alkyl, or R[1] and R[2] taken together represent

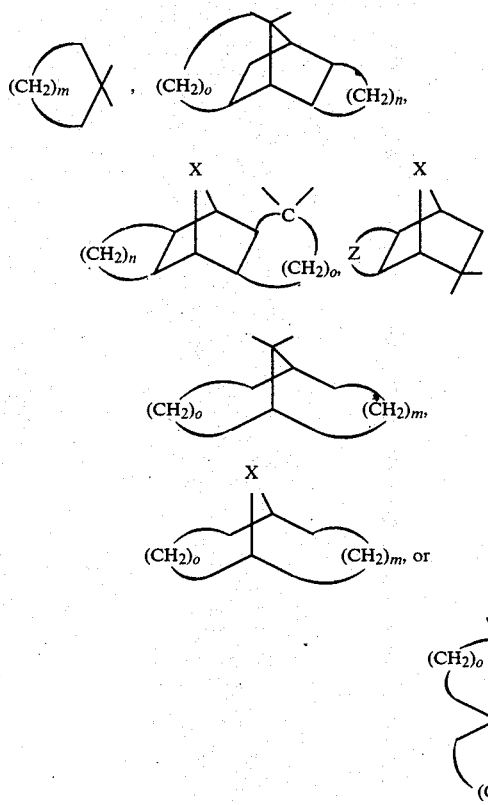

A is O or NR[3];
B is —(CH$_2$)$_n$—, $$-\underset{R^4}{\underset{|}{CH}}- \text{ or } =\underset{R^4}{C}-;$$

R[3] is hydrogen or lower alkyl;
R[4] is hydrogen, lower alkyl, aryl of 6-12 carbon atoms or halo;
R[5] is unsubstituted or substituted phenyl, 2-pyridinyl, 2-pyrimidinyl, 2-pyrazinyl or 3-pyridazinyl, where the substituents are selected from the group lower alkyl, lower alkoxy, halo, cyano, nitro and trifluoromethyl;

Z is —(CH$_2$)$_n$— or vinylene;
X is lower alkylene, vinylene or O;
m is 2-5;
n is 1-3;
o is 1-5;

and the pharmaceutically acceptable salts thereof.

The term "lower alkyl" refers to moieties having 1-6 carbon atoms in the carbon chain. The term "lower alkoxy" refers to moieties having 1-6 carbon atoms. The term "lower alkylene" refers to saturated moieties having 1-4 carbon atoms in the carbon claim. The term "halo" refers to fluoro, chloro and bromo.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of the invention may be prepared by a variety of synthetic routes using conventional methods.

Compounds of the invention can be prepared according to the following scheme illustrating the instance in which the compounds contain the moiety

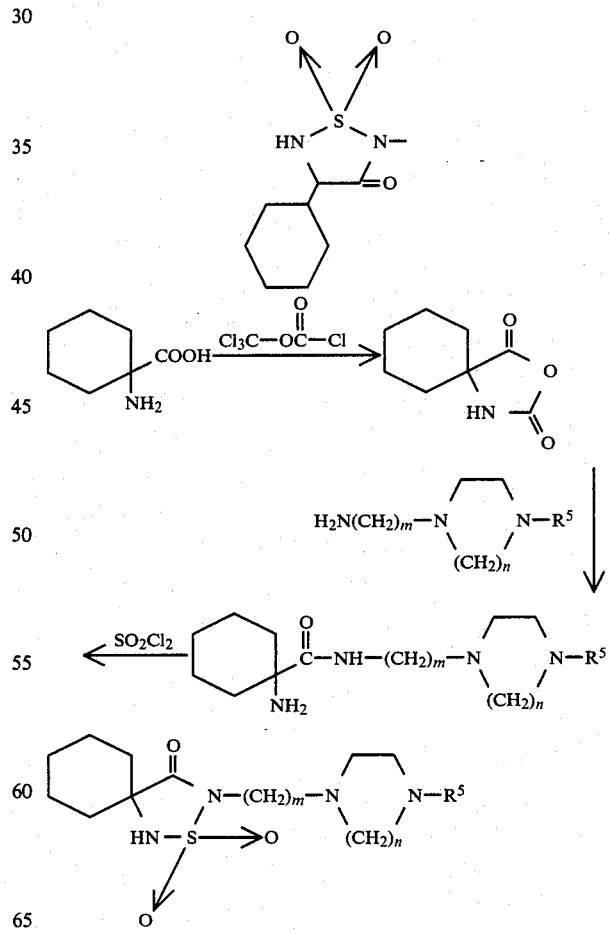

wherein R[5], m and n are as defined hereinbefore. In the above sequence, the various reaction steps are carried out in an organic solvent at room or elevated temperature.

In an alternative reaction sequence, compounds of the invention having, for example, the moiety

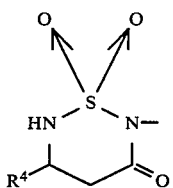

can be prepared by reacting a suitable thiadiazineone dioxide with an appropriate dihalo lower alkane to yield an intermediate

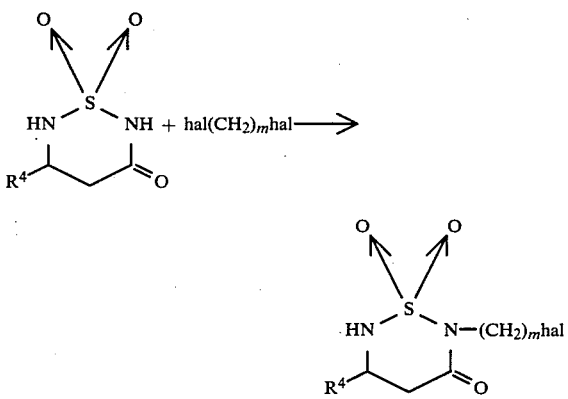

which is then reacted with, for example, an appropriately substituted 4-piperazine to yield the desired final product

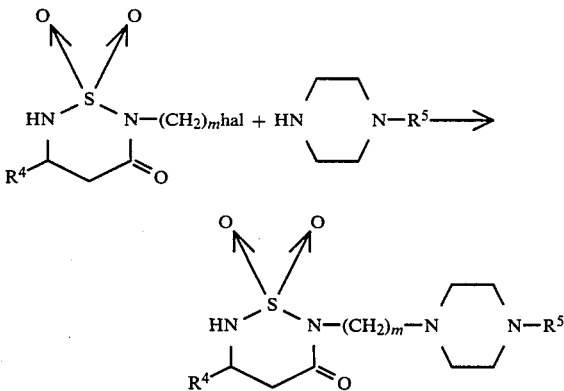

Again, the reaction steps are carried out in the presence of an organic solvent.

Of course, other methods of preparation, which will occur to those skilled in the art, may also be employed to prepare the compounds of the invention.

The starting materials used in the above-described preparative route are commercially available, or can be made according to procedures taught in the chemical literature.

The compounds of the invention may exist either in the form of the free base or the pharmacologically acceptable salts. Methods for converting one such form to another will be obvious to one skilled in the chemical arts.

The compounds of the invention display a pharmacological profile like that of the compound buspirone (8-[4-[4-(2-pyrimidinyl)-1-piperazinyl]butyl]-8-azaspiro[4.5]decane-7,9-dione). The latter compound has demonstrated preclinical activity in antipsychotic paradigms and has also displayed a unique clinical anxioselective profile, whereby its efficacy in the treatment of anxiety neuroses is comparable to the benzodiazepine diazepam but without the benzodiazepine-related side effects. The clinically effective anxiolytic doses of the benzodiazepines produce such undesirable side effects as ataxia, muscle relaxation and sedation. Additionally, most chronically used antipsychotic drugs, cause extrapyramidal side effects, such as pseudoparkinsonism, tardive dyskinesia and the like. Ideally, treatment of psychoses and anxiety should be free of any undesirable side effects. The compounds of the invention, in a manner similar to buspirone, display preclinical antipsychotic activity without or with minimal side effects. Moreover, based on their buspirone-like profile, the compounds of the invention can be considered of clinical value in treating anxiety neuroses.

When employed as anxiolytics/antipsychotics, the effective dosage of the substances active for such treatment will vary according to the particular compound being employed, the severity and nature of condition being treated. Therapy should be initiated at lower doses (in mg/kg/day), the dosage thereafter being increased, if necessary, to produce the desired effect. In general, the compounds of the invention are most desirably administered at a concentration that will generally afford effective results without causing any harmful or deleterious effects.

When the compounds of the invention are employed as anxiolytics/antipsychotic agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The antipsychotic activity of the compounds of the invention and their substantial lack of extrapyramidal side effects may be demonstrated by standard pharmacological procedures, which are described more fully in the examples given hereafter.

The following examples show the preparation and pharmacological testing of compounds within the invention.

EXAMPLE 1

2-[4-[4-(6-Chloro-2-pyrazinyl)-1-piperazinyl]butyl]-5,6-dihydro-5-methyl-2H-1,2,6-thiadiazin-3(4H)-one 1,1 dioxide To a stirred solution of 2.5 g (0.015 mol) of 5,6-dihydro-5-methyl-2H-1,2,6-thiadiazin-3(4H)-one 1,1-dioxide in 70 mL of dimethylformamide is added 0.7 g (0.03 mol) of sodium hydride. The resulting clear solution is added dropwise to a stirred solution of 4.3 g (0.02 mol) of 1,4-dibromobutane in 40 mL of dimethylformamide.

The reaction mixture is stirred overnight and the solvent is removed under vacuum and the residue is partitioned between methylene chloride and water. The combined methylene chloride extracts are combined, washed with brine and dried over anhydrous $Na_2SO_4$. Filtration and removal of the solvent in vacuo affords 4 g (88% yield) of 2-(4-bromobutyl)-5,6-dihydro-5-methyl-2H-1,2,6-thiadiazin-3(4H)-one 1,1-dioxide as yellow oil.

The title compound is prepared by adding to a stirred solution of 2 g (0.006 mol) of 2-(4-bromobutyl)-5,6-dihydro-5-methyl-2H-1,2,6-thiadiazin-3(4H)-one 1,1-dioxide in 50 mL of dimethylformamide, 4 mL of triethylamine and 1.41 g (0.006 mol) of 1-(6-chloro-2-pyrazinyl)piperazine hydrochloride.

The reaction mixture is stirred overnight and the solvent is removed under vacuum and is then partitioned between water and methylene chloride. The methylene chloride extracts are combined, washed with brine, dried over anhydrous $Na_2SO_4$, filtered and rotoevaporated to give crude free base. Preparative HPLC [silica gel, ethyl acetate:methylene chloride, (9:1)] followed by evaporation of the appropriate fractions (TLC $R_f$=0.6), treatment with ethanolic hydrogen chloride and recrystallization from ethanol gives the title compound; m.p. 107°–109° C.

Analysis for: $C_{16}H_{25}N_6ClSO_3 \cdot 2HCl \cdot \frac{1}{2}H_2O$; Calculated: C, 38.51; H, 5.65; N, 16.55. Found: C, 38.49; H, 5.46; N, 17.25.

EXAMPLE 2

3-[4-[4-(2-Pyrimidinyl)-1-piperazinyl]butyl]2-thia-1,3-diazaspiro[4,5]decan-4-one 2,2-dioxide To a stirred suspension of 1-amino-1-cyclohexanecarboxylic acid (2.5 g; 0.017 ml) in 70 mL of dioxane, is added 6 mL of trichloromethylchloroformate (TCF) and stirring is continued for 4 hours at 55° C. or until a clear solution is obtained (reaction time from 4 to 6 hours). Dioxane is evaporated under reduced pressure and the separated solid is analyzed by IR and NMR to be spiro[4,5]decan-2,4'-oxazolidine2,5'-dione. This compound is dissolved in 50 mL of methylene chloride and while stirring, 4.7 g (0.02 mol) of 1-(4-aminobutyl)-4-(2-pyrimidinyl)piperazine is added and stirring is continued for 3 hours at 50° C. The methylene chloride layer is washed with brine, dried over anhydrous $Na_2SO_4$ and evaporated under reduced pressure to afford 2 g of 2-amino-2-cyclohexyl-N-[4-[4-(2-pyrimidinyl)-]piperazinyl]acetanilide. The title compound is prepared by dissolving 2 g of 2-amino-2-cyclohexyl-N-[4-[4-72-pyrimidinyl)piperazinyl]acetanilide in 50 mL of methylene chloride, and to the stirred solution is added 2 mL of sulfuryl chloride and 4 mL of triethylamine. Stirring is continued at room temperature for 24 hours and the methylene chloride is washed with water, dried and rotoevaporated and the free base was separated via preparative HPLC [silica gel, ethyl acetate:methylene chloride (9:1)] followed by evaporation of the appropriate fractions and is converted to the dihydrochloride salt; m.p. 211°–214° C.

Analysis for: $C_{19}H_{30}SN_6O_3b \cdot 2HCl \cdot \frac{1}{2}H_2O$; Calculated: C, 45.24; H, 6.55; N, 16.67. Found: C, 45.98; H, 6.30; N, 16.49.

EXAMPLE 3

5,6-Dihydro-5-methyl-2-[4-[4-(2-pyrimidinyl)-1-piperazinyl]butyl]-2H-1,2,6-thiadiazin-3(4H)-one 1,1-dioxide The title compound is prepared following the procedure of Example 1 using 1-(2-pyrimidinyl)piperazine instead of 1-(6-chloro-2-pyrazinyl)piperazine hydrochloride and is converted to the hydrochloride salt; m.p. 115°–117° C.

Analysis for: $C_{16}H_{26}N_6SO_3 \cdot 2HCl \cdot H_2O$: Calculated: C, 40,59; H, 6.34; N, 17.76; Cl, 15.01. Found: C, 40,64; H, 6.22; N, 18.32; Cl, 15.46.

EXAMPLE 4

The compounds of the invention are tested in an assay to determine their ability to antagonise apomorphine-induced stereotyped behavior. The assay measures the in vivo dopamine receptor blocking activity of the compounds and provides a means for gauging whether the compounds tested may potentially exhibit extrapyramidal side effects.

The assay is carried out as follows:

20–25 gm male CF-1 mice (Charles River) are used. The mice are tested one week before the experiment for a positive stereotyped response to 10 mg/kg s.c. apomorphine. Test compounds, suspended or solubilized in 0.25% Tween 80 ® in water, are administered at several dose levels to male mice (6/dose level). A control group, run simultaneously with drug groups, receives equal volumes of solvent. Thirty minutes later (i.p. administration) or 60 minutes later (p.o. administration), drug-treated and control mice are challenged with 10 mg/kg apormorphine s.c.. Five minutes after the injection, the rearing-head-bobbing-licking syndrome induced by apomorphine is recorded as present or absent for each animal. Readings are repeated every 5 minutes during a 30 minute test session.

The number of positive or negative 5-minute intervals during which apomorphine-induced stereotyped behavior is present or absent is measured. $ED_{50}$ values (with 95% confidence intervals) are calculated for inhibition of apomorphine-induced stereotyped behavior, by a simple linear regression analysis with inverse prediction.

| Standard Compounds: | $ED_{50}$ and 95% confidence interval (mg/kg, intraperitoneal) |
|---|---|
| Haloperidol | 1.37 (0.88–2.34) |
| Chloropromazine | 8.48 (4.79–16.38) |
| Clozapine | 30.06 (19.42–48.21) |

The compounds of the invention, when tested in this assay are inactive, evidencing a low potential for exhibiting extrapyramidal side effects, such as pseudo parkinsonism, tardive dyskinesia and the like.

EXAMPLE 5

The ex vivo inhibition of 5-HT-1A serotonin receptor binding assay is used to determine whether the test compounds can cross the blood-brain barrier and affect the receptor in question and to give an indication of buspirone-like anxiolytic activity.

The assay is carried out as follows:

Several groups of rats (4–6 rats/group) are injected with test compound or the appropriate vehicle. Thirty minutes later, unless otherwise noted, rats are decapitated and their brains removed. Various brain regions are dissected and rapidly frozen and maintained at −70° C. until used.

Hippocampal tissue is dissected and homogenized on ice in 40 vols of buffer (50 mM Tris HCl, pH=7.7) using a Polytron homogenizer at setting 5 for 3×15 sec bursts. The homogenate is then centrifuged at 20,000 rpm (RC5-B; 50,000 g) and the supernatant discarded. The pellet is resuspended in 40 vols of the same buffer and incubated at 37° C. for 10 minutes to aid in the removal of endogenous serotonin. the homogenate is then centrifuged (as above) and the supernatant discarded. The pellet is then resuspended in 100 vols of buffer B (50 mM Tris HCl, pH=7.7 containing 0.1% ascorbate, 10 $\mu$M pargyline and 4 mM $CaCl_2$) and sonicated. An aliquot is taken for protein determination by the Lowry method and the remainder stored frozen at −70° C. until used.

The homogenate (50 $\mu$l; 0.4–0.6 mg protein/sample) is incubated with 100 $\mu$l (1.5–1.8 nM) $^3$H-8-hydroxy-2-(di-n-propylamino)tetraline in a final volume of 2 ml of buffer for 10 minutes at 37° C. At the end of the incubation, 3 ml of cold buffer A are added to each tube, and the contents rapidly filtered through Whatman GF/B glass filters. The filters are then rapidly washed 2 times with 3 ml of the same buffer, placed in scintillation vials, and shaken for 15 minutes with 10 ml of Hydrofluor (National Diagnostics) scintillation cocktail. The vials are then counted in a Packard 460 CD scintillation counter.

Specific binding is calculated for each of the treatment protocols and is defined as total binding less binding in the presence of excess unlabeled serotonin (1 $\mu$M). Specific binding obtained in vehicle-treated rats is compared to that obtained in animals receiving a single or various doses of test compound and expressed as percent of control. The use of several doses of test compound permits the calculation of an $ID_{50}$ value, i.e. an inhibitory dose that displaces 50% of the specific binding ex vivo.

Under these conditions, buspirone (30 mg/kg) displaced 46% of specific $^3$H-8-OH-DPAT binding from hippocampal membranes.

When tested in this assay, the compound of Example 1 displaced 61% of specific $^3$H-8-OH-DPAT binding from hippocampal membranes at 1 $\mu$M of drug concentration.

EXAMPLE 6

A test designed to determine the potential antipsychotic activity of the compounds of the invention is the conditioned avoidance (shelf-jump response) test.

This test is carried out as follows:

Male CD rats (Charles River) maintained at approximately 400–450 gm body weight are used. Previously trained rats are placed in plexiglass experimental chambers divided into two sections; a main chamber ($10\frac{1}{2}''\times6\frac{3}{4}''\times11\frac{7}{8}''$ high) and an elevated chamber or shelf ($5\frac{7}{8}''\times6\frac{7}{8}''\times5\frac{3}{4}''$). A moveable wall, controlled by a motor, determines whether the rat has access to the shelf at any time during the experiment. The experimental chamber also contains a house light and sonalert. A steel grid floor in the main chamber is wired for presentation of electric shock. Each trial consists of a fifteen-second warning tone (conditioned stimulus), continuing for an additional fifteen seconds accompanied by electric shock, (unconditioned stimulus). A response (jumping onto the exposed shelf of the upper chamber) occurring during the initial fifteen-second warning tone is considered an avoidance response, while a response occurring during shock delivery is considered an escape response. Trials are presented on a fixed interval schedule of one minute. The session consists of thirty-six trials. Animals are run twice weekly with control sessions always preceding a drug run, and with at least one day intervening. Compounds are administered i.p. or p.o. at appropriate pre-treatment times to a minimum of five rats at each dose level over a range of doses.

The following experimental parameters are recorded by computer: (1) the number of avoidance responses, (2) the number of escape responses, and (3) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance and the dose calculated to produce a 50% block in avoidance responding ($AB_{50}$) is obtained from a dose-effect regression line fitted by the method of least squares. Potential anti-psychotic compounds suppress avoidance responding and increase escape responding.

| Standard Compounds: | $AB_{50}$ (mg/kg i.p.) |
|---|---|
| Haloperidol | 0.19 |
| Chlorpromazine | 3.69 |
| Clozapine | 6.94 |
| Buspirone | 9.94 |

The results for compounds of this invention in this test are presented in Table 2.

TABLE 2

| Compound of Example No. | Active at (mg/kg) |
|---|---|
| 1 | 40 (i.p.)* |
| 2 | 40 (i.p.) |
| 3 | 40 (i.p.) |

*(i.p.) = intraperitoneally administered drug.

The results show that compounds of the invention are active intraperitoneally in this test.

EXAMPLE 7

The antipsychotic activity of the compounds of the invention is assessed via the conditioned avoidance (discrete trial) test. This test has excellent clinical correlation for antipsychotic activity.

The test is carried out as follows:

Male CD rats (Charles River) maintained at approximately 400–450 gm body weight are used. Rats trained previously are placed in plexiglass experimental chambers equipped with a response lever, house light, and sonalert. A steel grid floor is wired for presentation of electric shock. Each trial consists of a fifteen-second warning tone (conditioned stimulus), continuing for an additional fifteen seconds accompanied by electric shock, (unconditioned stimulus). The rat can terminate a trial at any point by depression of the response lever. As response during the initial fifteen-second warning tone ends the trial before shock delivery and is considered avoidance response, while a response occurring during shock delivery is an escape response. Trials are presented on a variable interval schedule of two minutes. The session consists of sixty trials. Animals are run two to three times weekly with control sessions always preceding a drug run, and with at least one day intervening, compounds are administered i.p. or p.o. at appropriate pre-treatment times to a minimum of five to six rats at each dose level over a range of doses.

The following experimental parameters are recorded by computer; (1) the number of interval responses, (2) the number of avoidance responses, (3) the number of escape responses, and (4) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance and the dose calculated to produce a 50% block in avoidance responding ($AB_{50}$) is obtained from a dose-effect regression line fitted by the method of least squares. Potential anti-psychotic compounds suppress avoidance responding and increase escape responding.

| Standard Compounds | $AB_{50}$ (mg/kg, peroral administration) |
| --- | --- |
| Buspirone | 47.9 (41.3-55.5) |

When tested in this assay, the compound of Example 1 gave an $AB_{50}$ of 32.45 when administered perorally, evidencing very significant activity.

What is claimed is:

1. A compound having the formula

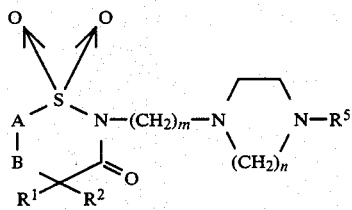

wherein $R^1$ and $R^2$ are each, independently, hydrogen or lower alkyl, or $R^1$ and $R^2$ taken together represent

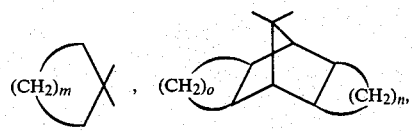

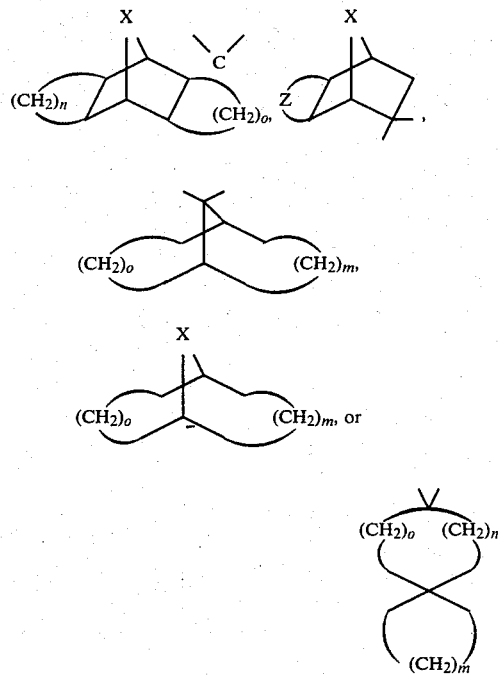

A is $NR^3$;

B is —$(CH_2)_n$—, $$-\underset{R^4}{CH}- \text{ or } =\underset{R^4}{C}-;$$

$R^3$ is hydrogen or lower alkyl;

$R^4$ is hydrogen, lower alkyl, or halo;

$R^5$ is unsubstituted or substituted phenyl, 2-pyridinyl, 2-pyrimidinyl, 2-pyrazinyl or 3-pyridazinyl, where the substituents are selected from the group lower alkyl, lower alkoxy, halo, cyano, nitro and trifluoromethyl;

Z is —$(CH_2)_n$— or vinylene;

X is lower alkylene, vinylene or O;

m is 2–5;

n is 1–3;

o is 1–5;

and the pharmaceutically acceptable salts thereof.

2. A compound having the formula

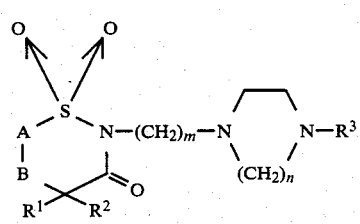

wherein $R^1$ and $R^2$ are each, independently, hydrogen or lower alkyl, or $R^1$ and $R^2$ taken together represent

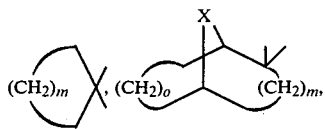

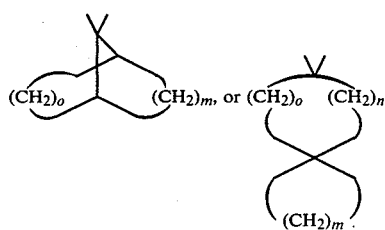

A is NR³;

B is —(CH₂)ₙ—,

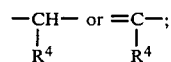

R⁵ is unsubstituted or substituted phenyl, 2-pyridinyl, 2-pyrimidinyl, 2-pyrazinyl or 3-pyridazinyl, where the substituents are selected from the group lower alkyl, lower alkoxy, halo, cyano, nitro and trifluoromethyl;

Z is —(CH₂)ₙ— or vinylene;
X is lower alkylene, vinylene or O;
m is 2–5;
n is 1–3;
o is 1–5;
and the pharmaceutically acceptable salts thereof.

3. The compound of claim 1, having the name 2-[4-[4-(6-chloro-2-pyrazinyl)-1-piperazinyl]butyl]-5,6-dihydro-5-methyl-2H-1,2,6-thiadiazin-3(4H)-one 1,1 dioxide.

4. The compound of claim 1, having the name 3-[4-[4-(2-pyrimidinyl)-1-piperazinyl]butyl]-2-thia-1,3-diazaspiro[4,5]decan-4-one 2,2-dioxide.

5. The compound of claim 1, having the name 5,6-dihydro-5-methyl-2-[4-[4-(2-pyrimidinyl)-1-piperazinyl]butyl]-2H-1,2,6-thiadiazin-3(4H)-one 1,1-dioxide.

* * * * *